(12) United States Patent
Moradi et al.

(10) Patent No.: US 10,018,712 B2
(45) Date of Patent: Jul. 10, 2018

(54) METHOD FOR IMPROVED ULTRASONIC DETECTION

(75) Inventors: Mehdi Moradi, Vancouver (CA);
Purang Abolmaesumi, Kingston (CA);
Parvin Mousavi, Kingston (CA); Eric Sauerbrei, Kingston (CA); Robert Siemens, Kingston (CA); Phillip Isotalo, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 423 days.

(21) Appl. No.: 12/227,697

(22) PCT Filed: May 25, 2007

(86) PCT No.: PCT/CA2007/000934
§ 371 (c)(1),
(2), (4) Date: Oct. 22, 2009

(87) PCT Pub. No.: WO2007/137411
PCT Pub. Date: Dec. 6, 2007

(65) Prior Publication Data
US 2010/0063393 A1    Mar. 11, 2010

Related U.S. Application Data

(60) Provisional application No. 60/808,557, filed on May 26, 2006.

(51) Int. Cl.
  *G01S 7/52*   (2006.01)
  *A61B 8/08*   (2006.01)
  *G01S 15/89*  (2006.01)
(52) U.S. Cl.
  CPC ........ *G01S 7/52036* (2013.01); *A61B 8/0833* (2013.01); *G01S 15/8977* (2013.01)

(58) Field of Classification Search
  USPC ....... 600/407, 437, 438, 439, 440, 441, 443, 600/444, 445, 446, 447, 449, 453, 454,
  (Continued)

(56) References Cited

U.S. PATENT DOCUMENTS 5,417,215 A * 5/1995 Evans .................. A61B 8/08
                                                  600/442
5,453,575 A    9/1995 O'Donnell
(Continued)

FOREIGN PATENT DOCUMENTS

WO    WO2007/137411    12/2007

OTHER PUBLICATIONS

"Relationship of Ultrasonic Spectral Parameters to Features of Tissue Microstructure" by F.L. Lizzi, M. Ostromogilsky, E.J. Feleppa, M.C. Rorke, and M.M. Yaremko. IEEE Trans. Ultra. Ferro. Freq. Control. vol. UFFC-33, No. 3, pp. 319-329. (1986).*
(Continued)

*Primary Examiner* — Tse Chen
*Assistant Examiner* — Jason Ip
(74) *Attorney, Agent, or Firm* — Stephen J. Scribner

(57) ABSTRACT

This invention relates to a method of analyzing an ultrasound signal. The method comprises obtaining a time series of sequential data frames associated with an ultrasound signal reflected from and/or backscattered from a fixed location of a material under investigation, each data frame comprising a plurality of samples of the ultrasound signal, and subjecting to an analysis a sequence of one or more samples of the ultrasound signal, or a sequence of at least one parameter derived from one or more samples of the ultrasound signal, wherein a result of the analysis is related to one or properties or characteristics of the material. In one (Continued)

embodiment the method may be used for detecting, diagnosing, and/or assessing cancer and/or abnormalities in biological tissue.

15 Claims, 8 Drawing Sheets

(58) Field of Classification Search
USPC ........ 600/462, 463, 464, 466, 467; 382/128; 128/915, 916
See application file for complete search history.

(56) References Cited

U.S. PATENT DOCUMENTS

| | | | |
|---|---|---|---|
| 6,056,691 | A | 5/2000 | Urbano |
| 6,312,382 | B1 | 11/2001 | Mucci |
| 6,508,768 | B1 | 1/2003 | Hall |
| 6,676,603 | B2 | 1/2004 | Aichhorn |
| 6,728,567 | B2 * | 4/2004 | Rather et al. ............ 600/407 |

OTHER PUBLICATIONS

"Probing the dynamics of tissue at low frequencies with the radiation force of ultrasound" by M. Fatemi and J.F. Greenleaf. Phys. Med. Biol. 45 (2000) pp. 1449-1464.*

"Incoherent imaging using continuous wave ultrasound. A preliminary study using bovine intervertebral discs" by H. Liang et al. European Journal of Ultrasound. 16. pp. 253-260 (2003).*

"Method of improved scatterer size estimation and application to parametric imaging using ultrasound" by M.L. Oelze et al. J. Acoustic Society of America. 112 (6) pp. 3053-3063. 2002.*

"Ultrasonic Spectral-Parameter Imaging of the Prostate" by E.J. Feleppa et al. International Journal of Imaging Systems and Technology. vol. 8, Issue 1. pp. 11-25. 1997.*

Feleppa, E.J., et al., "Typing of prostate tissue by ultrasonic spectrum analysis", IEEE Trans. on Ultrasonics, Ferroelectrics, and Frequency Control 43(4):609-619 (1996).

Foster, F.S., et al., "Advances in ultrasound biomicroscopy", Ultrasound in Med. & Biol. 26: 1-27 (2000).

Goss, S.A., et al., "Compilation of empirical ultrasonic properties of mammalian tissues. II.", Journal of Acoust. Soc. Am. 68(6): 93-108 (1980).

Houston, A.G., et al., "Prostate ultrasound image . . . lesions to assist biopsy", Proceedings of the 8th IEEE Sym. on Computer-Based Medical Systems p. 94-101 (1995).

Lee, W.L., et al., "Ultrasonic liver tissues classification by fractal feature . . . transform", IEEE Transactions on Medical Imaging 22: 382-392 (2003).

Lizzi, F.L., et al., "Statistics of ultrasonic spectral . . . examination", IEEE Transactions on Ultrasonics, Ferroelectrics, and Frequency Control, 44(4): 935-942 (1997).

Lizzi, F.L., et al., "Theoretical framework for spectrum analysis . . . characterization", Journal of the Acoustic Society of America 73: 1366-1373 (1983).

Ophir, J., et al., "Elastography: a quantitative method for imaging the elasticity of biological tissues", Ultrasonic Imaging 13(2): 111-134 (1991).

Pansera, F., "Fractals and cancer", Medical Hypotheses 42: 400 (1994).

Ristanovic, D., et al., "Fractal and nonfractal analysis of cell images: comparison . . . arborization", Biological Cybernetics 87: 278-288 (2002).

Sarkar, N., "An efficient differential box-counting approach to compute fractal dimension of image", IEEE Trans. Syst., Man, Cybern 24:115-120 (1994).

Scheipers, U., et al., "Ultrasonic multifeature tissue characterization for prostate diagnostics", Ultrasound in Medicine and Biology 20: 1137-1149 (2003).

Schmitz, G., et al., "Tissue characterization of the prostate using Kohonen-maps", Ultrasonics Symposium p. 1487-1490 (1994).

Schmitz, G., et al., "Tissue-characterization of the prostate . . . ultrasonic signals", IEEE Trans. on Ultrasonics, Ferroelectrics and Freq. Control 46: 126-138 (1999).

* cited by examiner (a: Bovine liver)

<br>
(b: Pig liver)

<br>
(c: Chicken breast)

<br>
(d: Bovine muscle)

METHOD FOR IMPROVED ULTRASONIC DETECTION

FIELD OF THE INVENTION

This invention relates generally to the field of ultrasound imaging. In particular, the invention relates to methods of analyzing radio frequency (RF) ultrasound signals for improved ultrasound imaging.

BACKGROUND OF THE INVENTION

Conventional inspection and examination of materials using ultrasound typically employs processing of the raw radio frequency (RF) ultrasound signal at discrete "snap-shots" in time, for example, to create B-scan images. Such images are widely used in fields such as medicine; however, evidence suggests that they may be of limited utility in certain applications, particularly where fine resolution of tissue structure is required for accurate classification, such as in-detecting structural differences among biological tissues, as may be required in diagnosing various cancers.

Several researchers have studied ultrasound-based solutions for computer-aided diagnosis of cancer. The first-order statistical moments (such as mean, standard deviation, skewness and kurtosis) of the intensities of pixels in each region of interest (ROI) of the tissue form a basic set of features for tissue classification [5, 6]. Tissue characterization based on the acoustic parameters extracted from the raw RF ultrasound echo signals (before being transformed to B-scan images) has been studied since the early 1970's (see [7] for a review). Frequency-dependent nature of ultrasound scattering and attenuation phenomena can characterize different tissue types and is studied through frequency spectrum of RF signals. Along with texture and co-occurrence based features extracted from B-scan images, RF spectrum parameters have been used to form hybrid feature vectors to be used for detection of cancer [20]. Such features are utilized as the input to neural networks and neuro-fuzzy inference systems [5], self organizing Kohonen maps [8] and quadratic Bayes classifiers [9] for characterization of tissue. Nevertheless, despite the long history of studies in this field, an accurate analytical model of ultrasound-tissue interactions is still outstanding [9, 10] and the results of RF-based tissue classification methods are not promising enough for clinical applications.

SUMMARY OF THE INVENTION

One aspect of the invention relates to a method for analyzing an ultrasound signal reflected from and/or back-scattered from a material, comprising:
  obtaining a time series of sequential data frames associated with the ultrasound signal from a fixed location of the material, each data frame comprising a plurality of samples of the ultrasound signal, and
  subjecting to an analysis:
    (i) a sequence of one or more samples of the ultrasound signal, or
    (ii) a sequence of at least one parameter derived from one or more samples of the ultrasound signal;
  wherein a result of the analysis is indicative of one or more physical properties of the material.
The data may be derived from a radio frequency (RF) ultrasound signal. In another embodiment, the data is derived from a processed ultrasound signal. The data may be derived from a processed ultrasound signal selected from an A-mode, B-mode, M-mode, Doppler, or 3-D ultrasound signal.

The analysis may be at least one selected from:
  (i) an analysis with respect to time, frequency, amplitude, or a combination thereof,
  (ii) a statistical analysis,
  (iii) a stochastic analysis,
  (iv) a fractal analysis;
  (v) a wavelet analysis;
  (vi) a spectral analysis;
  (vii) array processing; and
  (viii) a combination of two or more of the above.

In one embodiment, the analysis is fractal analysis.

The result of the analysis may be indicative of the physical property of the material being normal or abnormal. In another embodiment, the result of the analysis is a probability map or a probability score. The result of the analysis may be indicative of severity of the abnormality in the material. The result of the analysis may describe the presence of the abnormality in the material.

The material may be biological tissue. In one embodiment, the biological tissue is human biological tissue. In another embodiment, the material is biological tissue and the abnormality in the biological tissue is cancer. The cancer may be associated with at least one of female genital tract (ovary, fallopian tube, uterus, cervix and vagina), male genital tract (prostate and testis), urinary tract (kidney, ureter and prostate gland), mediastinum and heart, gastrointestinal tract. (small and large intestines, liver, pancreas, gallbladder and biliary system), breast, skin, nervous system, endocrine organs (thyroid gland, adrenal gland), head and neck region, lymph nodes, soft tissue, respiratory system (including lung), and combinations thereof. In another embodiment, the cancer is prostate cancer.

In another embodiment, the material is biological tissue and the abnormality in the biological tissue is selected from benign tumour, infection, abscess, necrosis, infarct, and combinations thereof.

The analysis may comprise subjecting the RF time series data to a discrete Fourier transform. The at least one parameter may be selected from:
  (i) average of magnitudes of coefficients of the discrete Fourier transform of the RF time series in a low frequency portion of the transformation;
  (ii) average of magnitudes of coefficients of the discrete Fourier transform of the RF time series in a mid-low frequency portion of the transformation;
  (iii) average of magnitudes of coefficients of the discrete Fourier transform of the RF time series in a mid-high frequency portion of the transformation;
  (iv) average of magnitudes of coefficients of the discrete Fourier transform of the RF time series in a high frequency portion of the transformation;
  (v) intercept of a line fitted to magnitudes of coefficients of the discrete Fourier transform of the RF time series plotted versus normalized frequency; and
  (vi) slope of a line fitted to magnitudes of coefficients of the discrete Fourier transform of the RF time series plotted versus normalized frequency.

Another aspect of the invention relates to a method for detecting, diagnosing, and/or assessing cancer, comprising:
  obtaining a time series of sequential data frames associated with an ultrasound signal reflected from and/or backscattered from a fixed location of a biological tissue, each data frame comprising a plurality of samples of the ultrasound signal, and subjecting to an analysis:
  (i) a sequence of one or more samples of the ultrasound signal, or
  (ii) a sequence of at least one parameter derived from one or more samples of the ultrasound signal;
wherein a result of the analysis is related to the detection, diagnosis, and/or assessment of cancer in the biological tissue.

In accordance with this aspect, the data may be derived from a RF ultrasound signal. In another embodiment, the data is derived from a processed ultrasound signal. The data may be derived from a processed ultrasound signal selected from an A-mode, B-mode, M-mode, Doppler, or 3-D ultrasound signal. The analysis may be at least one selected from:
  (i) an analysis with respect to time, frequency, amplitude, or a combination thereof,
  (ii) a statistical analysis,
  (iii) a stochastic analysis,
  (iv) a fractal analysis;
  (v) a wavelet analysis;
  (vi) a spectral analysis;
  (vii) array processing; and
  (viii) a combination of two or more of the above.

In one embodiment, the analysis is fractal analysis.

In accordance with this aspect, the cancer may be associated with at least one of female genital tract (ovary, fallopian tube, uterus, cervix and vagina), male genital tract (prostate and testis), urinary tract (kidney, ureter and prostate gland), mediastinum and heart, gastrointestinal tract (small and large intestines, liver, pancreas, gallbladder and biliary system), breast, skin, nervous system, endocrine organs (thyroid gland, adrenal gland), head and neck region, lymph nodes, soft tissue, respiratory system (including lung), and combinations thereof. In one embodiment, the cancer is prostate cancer.

Another aspect of the invention relates to programmed media for use with a computer and with an ultrasound signal, the programmed media comprising:
  a computer program stored on storage media compatible with the computer, the computer program containing instructions to direct the computer to perform one or more of:
  obtain a time series of sequential data frames associated with the ultrasound signal from a fixed location of the material, each data frame comprising a plurality of samples of the ultrasound signal;
  subject to an analysis:
    (i) a sequence of one or more samples of the ultrasound signal, or
    (ii) a sequence of at least one parameter derived from one or more samples of the ultrasound signal;
  determine one or more properties of the material based on a result of the analysis, and
  output an indication of the one or more properties.

The computer program may further direct the computer to:
  accept data relating to known properties of the same material, or complementary data from subsequent analysis conducted on the same material; and
  update the result of the analysis based on a comparison to the data relating to known properties of the same material and/or the complementary data.

In accordance with this aspect, the data may be derived from a RF ultrasound signal. In another embodiment, the data is derived from a processed ultrasound signal.

The data may be derived from a processed ultrasound signal selected from an A-mode, B-mode, M-mode, Doppler, or 3-D ultrasound signal.

Another aspect of the invention relates to a system for determining one or more properties of a material, comprising:
  a computer;
  the programmed media described above; and
  an ultrasound device for generating an ultrasound signal from the material.

Another aspect of the invention relates to a method for analyzing an ultrasound signal reflected from or transmitted through a material, comprising:
  obtaining a time series of continuous data frames associated with the ultrasound signal from a specific location of the material, each data frame comprising a plurality of ultrasound samples, and
  subjecting one or more samples of each said data frame to an analysis;
  wherein a result of the analysis is indicative of one or more physical properties of the material.

Another aspect of the invention relates to a method for measuring a physical property of a material, comprising:
  obtaining a time series of continuous data frames of an ultrasound signal reflected from or transmitted through a specific location of the material, each data frame comprising a plurality of ultrasound samples, and
  subjecting one or more samples of each said data frame to an analysis;
  wherein a result of the analysis is indicative of the physical property of the material.

The data may be derived from the raw RF ultrasound signal, or from a processed ultrasound signal such as an A-mode, B-mode, M-mode, Doppler, or 3-D ultrasound signal.

The specific location may be at a fixed location on the material.

In various embodiments, the analysis may be at least one analysis selected from:
  (i) an analysis with respect to time, frequency, amplitude, or a combination thereof,
  (ii) a statistical analysis,
  (iii) a stochastic analysis, and
  (iv) a combination of (i), (ii), or (iii).

In one embodiment, the result of the analysis is indicative of the physical property of the material being normal or abnormal. In another embodiment, the result of the analysis is a probability map or a probability score. In another embodiment, the result of the analysis is indicative of severity of the abnormality in the material. In another embodiment, the result of the analysis describes the presence of the abnormality in the material.

The material may be biological tissue. In one embodiment, the biological tissue is human biological tissue. In another embodiment, the biological tissue is prostate tissue.

In another embodiment, the abnormality in the biological tissue may be cancer. The cancer may be prostate cancer, breast cancer, liver cancer, lung cancer, skin cancer, or ovarian cancer. In another embodiment, the cancer is prostate cancer.

In one embodiment, the fractal analysis is the Higuchi method.

According to another aspect of the invention there is provided a method for diagnosing cancer, comprising:
  obtaining a time series of continuous data frames associated with an ultrasound signal reflected from a specific location of a biological tissue, each data frame comprising a plurality of ultrasound samples, and subjecting one or more samples of each said data frame to an analysis;

wherein a result of the analysis is related to the probability of cancer in the biological tissue.

The data may be derived from the raw RF ultrasound signal, or from a processed ultrasound signal such as an A-mode, B-mode, M-mode, Doppler, or 3-D ultrasound signal.

The analysis may be at least one analysis selected from:
(i) an analysis with respect to time, frequency, amplitude, or a combination thereof,
(ii) a statistical analysis,
(iii) a stochastic analysis, and
(iv) a combination of (i), (ii), or (iii).

The analysis may include the Higuchi method.

The cancer may be prostate cancer, breast cancer, liver cancer, lung cancer, skin cancer, or ovarian cancer. In one embodiment, the biological tissue is prostate tissue and the cancer is prostate cancer.

BRIEF DESCRIPTION OF THE DRAWINGS

Embodiments of the invention will now be described, by way of example, with reference to the drawings, wherein.

DETAILED DESCRIPTION OF ILLUSTRATIVE EMBODIMENTS

Figure 1:
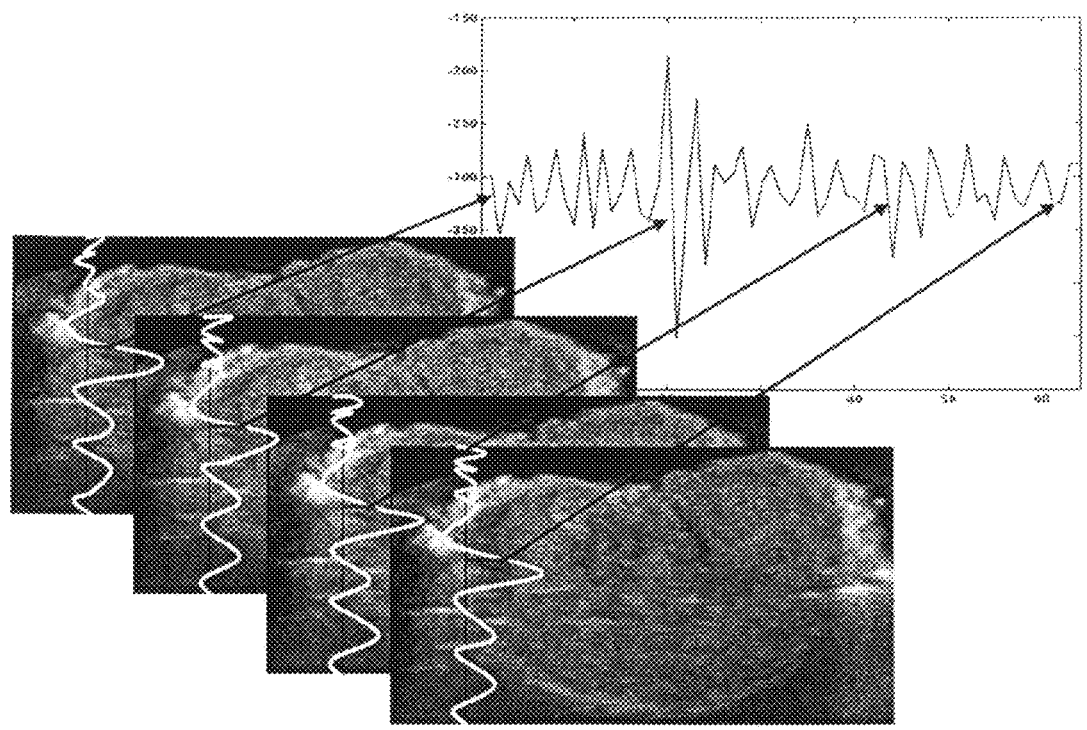
FIG. 1 is a graphical representation showing how the time series data was acquired.

As a new approach toward a more accurate classification of materials, detection, assessment, and/or diagnosis of abnormalities, imperfections, and/or defects in materials, based on ultrasound RF signals, we considered that the interaction of the material and ultrasound may be studied through a stochastic or fractal analysis and described by, for example, fractal features. We proposed that the RF output of such a system could result in a fractal pattern when recorded as a time series (a fractal curve or signal has the property that each part of it can be considered as an image of the whole in a reduced scale). We therefore obtained raw ultrasound RF data (i.e., the ultrasound RF signal prior to any processing) and subjected it to time series analysis.

The idea that the interaction of the material and ultrasound may be studied through a stochastic or fractal analysis is particularly relevant to biological tissues. This is based on the fact that self-organizing self-replicating cells are the building blocks of biological tissues; furthermore, non-linearity and quasi-determinism are the basic properties of biological systems [11]. These two conditions are prerequisites for such analyses. The self-organizing and self-replicating properties result in a fractal pattern in their output when recorded as a time series. For example, it has been shown that gland-like structures in some types of adenocarcinoma possess a meaningful fractal dimension [12, 13].

To generate time series data for analysis, we acquired a continuous set of frames of RF data, at a specified frame rate, from a fixed location of the material. The RF data was digitized to facilitate analyses. However, the analyses described herein may be performed in digital or analogue domains, or in a combination of both domains. The data may also be derived from a processed ultrasound signal such as, for example, an A-mode, B-mode, M-mode, Doppler, or 3-D ultrasound signal. It will be appreciated that the methods described herein are also applicable to multi-frequency ultrasound, where harmonic imaging is possible. The methods described herein are also applicable to array signal processing, such as, for example, where single transmit and multiple receive channels are employed. In such embodiments, if suitable, the ultrasound signal can be discretized in time and/or amplitude and then subjected to processing.

As used herein, the term "continuous set of frames" refers to a sequential set of frames, in which an initial frame is followed in time by a subsequent frame or frames.

As used herein, the term "fixed location" refers to a location in or on the material under investigation relative to the ultrasound probe. That is, the probe is not moved but instead is maintained at a fixed location in or on the material under investigation. In addition, as used herein, the term "fixed" is intended to refer to the fact that the material is not subjected to any intentional movement, other than any minute movement of the material that might arise as a byproduct of interaction of the material with the ultrasound signal. In this regard the method described herein is distinct from the technique known as "elastography", in which gross movement of the material under investigation is intentionally induced through exposure to a high power ultrasound and/or mechanical signal.

It will be appreciated that the positional accuracy of the fixed location is subject to some uncertainty, however, which may arise through, for example, vibration of the probe and/or the material under investigation, such vibration being caused by, for example, vibration of the building, or movement of the tissue arising from a patient's breathing, heart beat, and/or pulse. Where such unintentional movement of the material occurs, the data may be processed to remove or compensate for such movement.

As used herein, the term "biological tissue" is intended to be inclusive of any tissue derived from an organism or part thereof, as well as a cell culture and a tissue culture. The biological tissue may be living or dead, and an analysis as described herein may be carried out on biological tissue in vivo or in vitro.

The material under investigation, which may be biological tissue, may be normal or abnormal, where "normal" refers to one or more properties or characteristics of the material falling within a range of acceptable values or meeting an acceptable value, or meeting a standard. "Abnormal" refers to one or more properties or characteristics of the material falling outside of a range of acceptable values or not meeting an acceptable value, or not meeting a standard. Where a normal material is being investigated, the investigation might include assessing one or more properties or characteristics of the material. Such assessment can be of interest in, for example, comparing one or more properties or characteristics of the material to one or more corresponding properties or characteristics of another material.

Within each digitized frame a region of interest (ROI) was defined, the size of the ROI being set as appropriate for the type of material being studied (see, for example, the below discussion and Examples). The ROI is in a fixed location in the series of frames, and is comprised of a matrix (e.g., 24×88) of samples, each sample representing a scalar value (e.g., amplitude) of the ultrasound RF signal. The temporal sequence of values corresponding to a sample in the matrix forms a time series. This is shown graphically in FIG. 1. Such time series data may then be subjected to a "single point" time series analysis, wherein one or more properties of that time series is determined. The analysis may be conducted with respect to, for example, time, amplitude, frequency, and combinations thereof such as time and frequency, and/or may include any mathematical operation or manipulation, and may include, but is not limited to, power spectrum, shift in central frequency, Fourier analysis, filtering, matrix or vector mathematics, wavelet, zero crossing, cyclic minima and maxima, phase analysis, data reduction (extract regions of data, concatenate, replicate, merge, interpolate, and decimate data series), mathematical functions (basic mathematical functions (addition, subtraction, multiplication, division) and/or integration, differentiation, logarithmic functions, trigonometric functions, exponential functions), or a statistical analysis such as, but not limited to, mean, variance, standard deviation, least squares fit, regression, Bayesian, RMS (root mean square), polynomial or linear curve fitting, correlation, autocorrelation, filtering (e.g., low pass, high pass, median), or a stochastic analysis such as, but not limited to probability distribution fitting, probability determination, signal/noise ratio, and fractal analysis, and combinations thereof. A set of such property values, which may be generated from any or all of the time series resulting from each sample in the ROI, may then be subjected to further analyses such as an analysis with respect to, for example, time, amplitude, frequency, and/or may include any mathematical operation or manipulation, such as, for example, a statistical or stochastic analysis as listed above.

Alternatively, in a "multi-point" time series analysis, the values of two or more samples from within a single ROI, each sample representing a scalar value (e.g., amplitude) of the ultrasound RF signal, may first be subjected to an analysis wherein a property of that ROI is determined. The analysis may include any mathematical operation or manipulation, such as, for example, a statistical or stochastic analysis, examples of which are noted above, to generate a property for that ROI. This analysis is repeated for that ROI in the time series, and the resulting time series of such properties may then be subjected to further analysis such as the single point analysis described above. A preferred fractal analysis is that proposed by Higuchi [14], which is a stable method to compute the fractal dimension of the irregular output time series of natural phenomena which show a turbulent behavior. However, the invention is not limited thereto.

Embodiments of the invention provide an enhanced ability to detect defects, abnormalities, and the like, in certain characteristics or properties of a material, and the extent or degree of severity of the defects, abnormalities, etc. in the material. For example, a property may be described as "abnormal" if the value(s) representing that property falls outside of a range of preferred values. Such characteristics or properties, of which there may be one or more for a given material and type of investigation, may include, for example, physical properties such as structure, elasticity, density, optical, and electromagnetic. For example, in the case of biological tissue, an abnormality may be detected in the arrangement of cells, relative to normal tissue of the same type, as is the case in many types of cancer. In non-biological materials, an abnormality may be detected as, for example, a variation in size or arrangement of pores, a variation in thickness or consistency of laminates, or a variation in density, relative to preferred values, or a minute crack or fissure in a material. Embodiments of the invention may allow input and storing of data relating to normal and abnormal characteristics of a material, and comparison of data for a current sample to the input/stored data, and as an output provide an indication (e.g., a probability) of whether the material is either normal or abnormal. Embodiments of the invention may also provide an indication as to extent or severity of the abnormality based on, for example, size, and/or location of the abnormality, and may further provide an indication of the grading of the abnormality (e.g., as is known for various cancers). One aspect of the invention provides for ongoing training of the method to recognize abnormalities by inputting data relating to examples of normal and/or abnormal material as such data become available, and by correcting the result based on supporting confirmatory or complementary data.

To demonstrate the effectiveness of the embodiments described herein, we have applied them to ultrasound data of biological tissue for diagnosing prostate cancer and for distinguishing different tissue types (see the below Examples). However, it will be appreciated that embodiments of the invention are not limited thereto, and they may be applied not only to other tissues for detection, diagnosis, and/or assessment of other cancers in any anatomic site, such as, but not limited to, female genital tract (ovary, fallopian tube, uterus, cervix and vagina), male genital tract (prostate and testis), urinary tract (kidney, ureter and prostate gland), mediastinum and heart, gastrointestinal tract (small and large intestines, liver, pancreas, gallbladder and biliary system), breast, skin, nervous system, endocrine organs (thyroid gland, adrenal gland), head and neck region, lymph nodes, soft tissue, respiratory system (including lung). Embodiments of the invention may also be used for detection, diagnosis, and/or assessment of tissue abnormalities including pathological abnormalities other than cancer, such as, but not limited to, benign tumours, infection, abscess, necrosis, and infarcts.

Embodiments of the invention may also be used for inspection and/or assessment of non-biological materials. Such applications may include inspection of materials for manufacturing and/or structural defects, analysis of effects of stress/strain on machine components, and detecting failure of machine components, in manufacturing, research, and industries such as transportation and aerospace.

Embodiments of the invention are further described by way of the following non-limiting examples.

Example 1

Detection of Prostate Cancer using Fractal Analysis 1.1 Introduction

Prostate cancer (PCa) is the most common malignancy among men and the second leading cancer-related cause of death after lung cancer [1]. It is estimated that there will be about 241,190 new cases of prostate cancer in North America in 2007 and about 31,350 men will die of this disease [2, 3]. If diagnosed in early stages, PCa is a manageable condition in many cases. However, the process of screening and diagnosis of the disease is controversial [4]. Prostate tumors have inconsistent appearances on medical images. In particular, on transrectal ultrasound (TRUS) which is the standard imaging modality to study prostate, cancer lesions can be hypoechoic, hyper-echoic or even isoechoic. The presence of benign prostatic hyperplasia (BPH) further complicates the visual inspection of ultrasound images, as BPH is typically associated with hyperplastic nodules that may mimic areas of malignancy.

The standard for detection of PCa is pathological analysis of tissue samples acquired through TRUS guided biopsy. However, the multi-focal nature of the disease and limited biopsy sampling of prostate cancer causes high rates of false negative diagnoses. Several researchers have studied ultrasound-based solutions for computer-aided diagnosis of PCa. The first-order statistical moments (such as mean, standard deviation, skewness and kurtosis) of the intensities of pixels in each region of interest (ROI) of the tissue form a basic set of features for tissue classification [5, 6]. Tissue characterization based on the acoustic parameters extracted from the raw RF ultrasound echo signals (before being transformed to B-scan images) has been studied since the early 1970's (see [7] for a review). Frequency-dependent nature of ultrasound scattering and attenuation phenomena can characterize different tissue types and is studied through frequency spectrum of RF signals. Along with texture and co-occurrence based features extracted from B-scan images, RF spectrum parameters have been used to form hybrid feature vectors to be used for detection of prostate cancer. Such features are utilized as the input to neural networks and neuro-fuzzy inference systems [5], self organizing Kohonen maps [8] and quadratic Bayes classifiers [9] for characterization of prostate tissue. Nevertheless, despite the long history of studies in this field, an accurate analytical model of ultrasound-tissue interactions is still outstanding [9, 10] and the results of RF-based tissue classification methods are not promising enough for clinical applications.

Figure 2A:
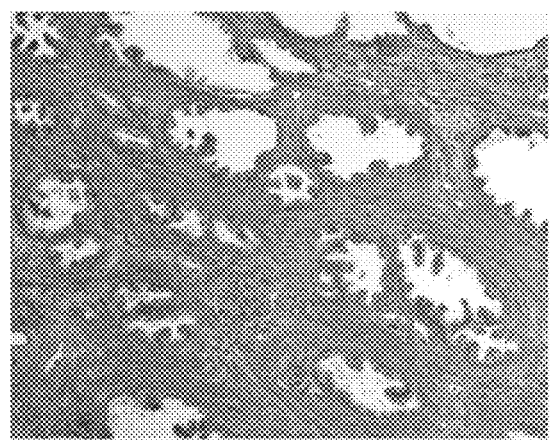
FIG. 2 shows typical microscopic images illustrating (a) normal prostate tissue, (b) benign prostatic hyperplasia tissue, and (c) prostatic carcinoma, as detected by an embodiment of the invention.
Figure 2B:
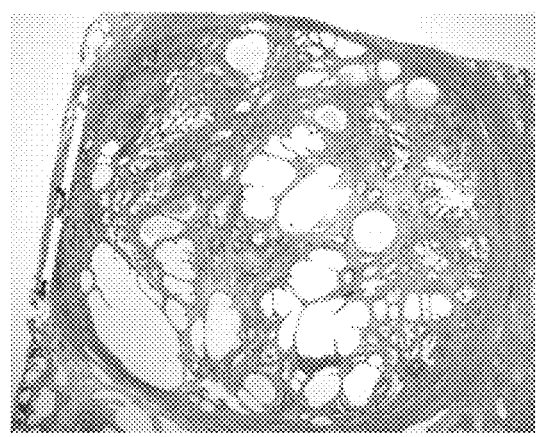
Figure 2C:
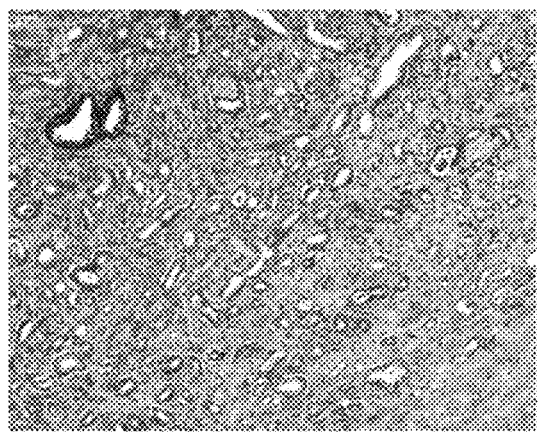

In prostate cancer, the progression of the malignancy is associated with geometrical deregulation of the architectural structure of the cellular network. This is in fact the basis for pathologic indices used for detecting and grading of the disease. FIG. 2 shows the typical appearances of the normal and cancerous tissue in pathology slides where the irregularity of the cancerous structure is vivid. It is also known that backscattered ultrasound signal is affected by the geometry and spatial distribution of scatterers [15]. Based on these two facts we examined the hypothesis that if the prostate tissue continuously undergoes interactions with the ultrasound signal, the time series formed by each sample of backscattered signal will have a fractal dimension which can be used to distinguish between cancerous and normal tissue.

To examine the validity of this hypothesis, we acquired continuous RF data frames from the prostate tissue of patients undergone radical prostatectomy, and extracted the Higuchi fractal dimensions of the time series formed in ROIs of size 0.028 cm$^2$ (the highest resolution ever reported). We analyzed the separability capability of this parameter between cancerous and normal tissue and found it to be statistically significant. Furthermore, we used neural networks to classify the ROIs and observed that when the Higuchi fractal dimensions of the RF time series is added to a combination of B-scan based texture features, the accuracy of neural network based classification of prostate tissue increases considerably. In fact, contrary to the fractal dimension of the B-scan ROIs which reportedly [16] performs as "another" texture feature, the Higuchi dimension of the time series of RF samples (averaged over the ROI) has a distinctive effect on the classification results.

1.2 Methods 1.2.1 Data

Figure 3A:
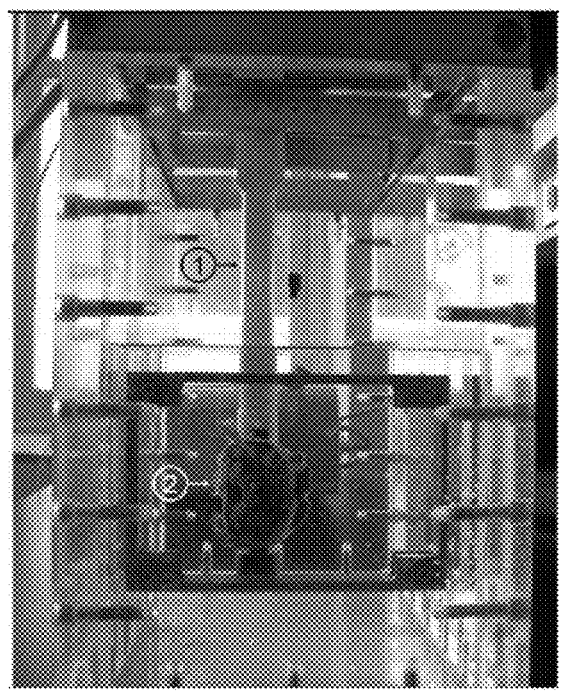
FIG. 3 shows the set-up for acquisition of the RF signal and B-scan image: (a) the probe (marked with 1 in the image) and prostate tissue (marked with 2 in the image) are fixed in position for continuous acquisition of the RF time series; (b) the first imaging position is marked with a needle (visible in the ultrasound image).
Figure 3B:
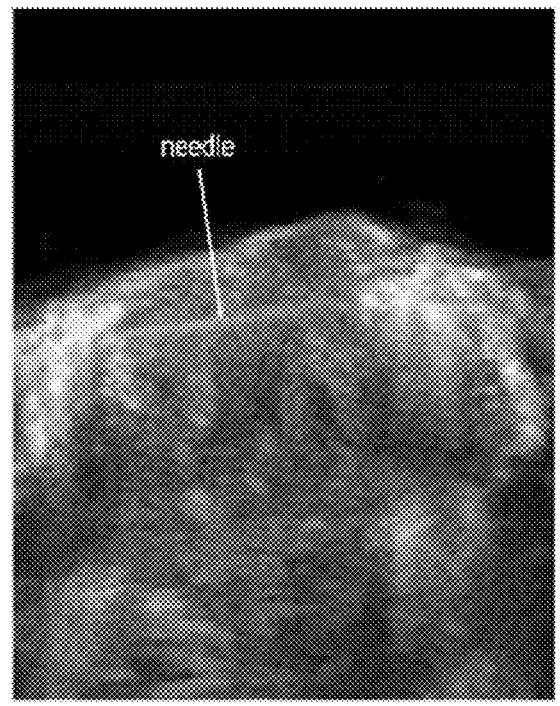

For ultrasound data collection, we used a Sonix RP (Ultrasonix Inc., Vancouver, Canada) ultrasound machine which has the capability of collecting and recording the raw RF signals, and an endorectal probe model BPSL9-5/55/10, frequency range: 5-9 MHz, set to 6.6 MHz for our experiments, and the linear transducer on this probe which is 55 nun long. FIG. 3(a) shows the data collection setup; the endorectal probe was mounted on a rail which could be moved along the prostate tissue while the tissue was fixed in a frame and immersed in water. We ensured that the orientation of the acquired ultrasound frames was as close as possible to the orientation of the slices to be made for specimen histopathologic analysis. To mark the position of the first ultrasound frame which had to be used as the origin for the pathological analysis, we placed a needle inside the tissue which was visible within the ultrasound image (FIG. 3(b)).

The Sonix RP machine was set to provide a maximum of 63 RF frames collected with the a rate of 8 frames per second. Each RF frame (equivalent to one B-scan image) consisted of 256 lines of RF signal each with 2064 samples (samples are the outputs of a 16 bit A/D converter operating at a frequency of 40 MHz). At each position we acquired 63 RF frames. The positions were 1 mm apart from each other. The size of ROIs used in this study was 16×16 pixels on the B-scan ultrasound which was equivalent to 0.028 cm$^2$ of the actual tissue or a window of size 24×88 in the equivalent RF frame. A total of four prostates were scanned and data acquired from two patients were used in this study. After acquisition of ultrasound data, a detailed histopathologic analysis was performed on tissue slices each 5 mm apart. Multifocal prostatic carcinoma was confirmed histologically in each prostate examined. Based on tissue histology, malignancy maps were produced for each prostate slice and were used as the standard for validation in this study.

1.2.2 Features

Every ROI was described with seven features:

four statistical moments of the pixel intensities in the B-scan image (mean, standard deviation, skewness and kurtosis);

box-counting fractal dimension of the corresponding window of the B-scan image (referred to hereinafter as "DBS"), and the box-counting fractal dimension of the corresponding window in the RF data (referred to hereinafter as "DRF"); and the average of Higuchi fractal dimensions of the RF sample time series in the ROI (referred to hereinafter as "AHDRFT" (average Higuchi dimension of RF time series)).

Single-frame-based fractal dimensions: DBS and DRF were extracted from a single B-scan image and the corresponding RF frame. For calculating three of DBS, we closely followed the box-counting method to compute the fractal dimension of a grayscale image (as described in [17] and also used in [18]). For computation of DRF, the RF frame was considered as a 2D matrix of gray levels and the same methodology as in [17] was applied.

Higuchi fractal dimension (AHDRFT) [14]: Consider N frames of RF data acquired at a regular rate while the probe and the tissue are fixed in position. Each sample of the RF data forms a time series X(1), X(2), . . . , X(N).

From this time series we first construct k new time series $X_k^m$ as follows:

$$X_k^m: X(m), X(m+k), X(m+2k), \ldots, X\left(m + \left[\frac{N-m}{k}\right] \cdot k\right)$$

where k<N, m=1, 2, . . . , k−1 and both are integers. The length of each time series is defined as:

$$L_m(k) = \frac{1}{k} \times \left(\frac{N-1}{\left[\frac{N-m}{k}\right] \cdot k}\right) \times \sum_{i=1}^{\left[\frac{N-m}{k}\right]} \left| X(m+ik) - X(m+(i-1) \cdot k) \right|. \quad (1)$$

The average value of Lm(k) over k sets (denoted with <L(k)>) is the length of the curve. If the condition <L(k)>∝k$^{-d}$ holds, the curve is fractal with the dimension d. In other words, to compute d, a line is fitted to values of ln (Lm(k)) versus ln (1/k) and the slope of this line is considered as the Higuchi fractal dimension of the time series. In our implementation, k=16 and N=64 (the 63 point time series was augmented with one sample equal to the last sample to increase the computational efficiency). AHDRFT is the average of d value computed for all the RF samples in the corresponding RF window of an ROI.

1.2.3 Class Separability Measure of the Features

One of the classical measures to quantify the separability capabilities of individual features in a two class problem is the so-called Fisher's Discriminant Ratio (FDR) [19]:

$$FDR = \frac{\mu_1 - \mu_2}{\sigma_1^2 + \sigma_2^2} \quad (2)$$

where $\mu_1$ and $\sigma_1^2$ are the mean and the variance of the values of the feature in class one respectively. Value of FDR is a statistical measure of the capability of the feature to discriminate the samples from the two classes. A higher value of FDR is an indication of higher separability capability of the feature.

1.2.4 Classification

We performed several classification experiments with artificial neural networks (ANN). We applied multi layer perceptron networks (feedforward) with one or two hidden layers and used different combinations of the seven features described in section 1.2.2 as their input. Back propagation was used for training the networks. Trained networks were tested on separate unseen ROIs and the results were validated based on the histopathologic analysis of the tissue. In one set of experiments, data acquired from one patient was used for training and testing the networks. In the second set of experiments, networks were trained on one patient and tested on another one.

1.3 Results

Statistical analysis of separability capability of features: Table 1.1 summarizes the FDR values for the two more effective statistical moments, as well as DBS, DRF and AHDRFT. Separability capability of AHDRFT is clearly higher compared to all other features. In addition, the value of correlation coefficient of AHDRFT with mean is significantly lower than the correlation coefficients of DBS and DRF with mean. This can be an indication of the independence of AHDRFT from the absolute pixel intensities in the ROI which is a useful property for dealing with isoechoic tumors.

TABLE 1.1

The FDR of features and their correlation coefficient with feature "mean".

| Feature | Fisher's discriminant ratio | Correlation with mean |
|---|---|---|
| mean | 5.8 | — |
| std | 26.6 | 0.3401 |
| DBS | 339.9 | 0.9932 |
| DRF | 132.8 | 0.9627 |
| AHDRFT | 1186.7 | 0.4552 |

Figure 4A:
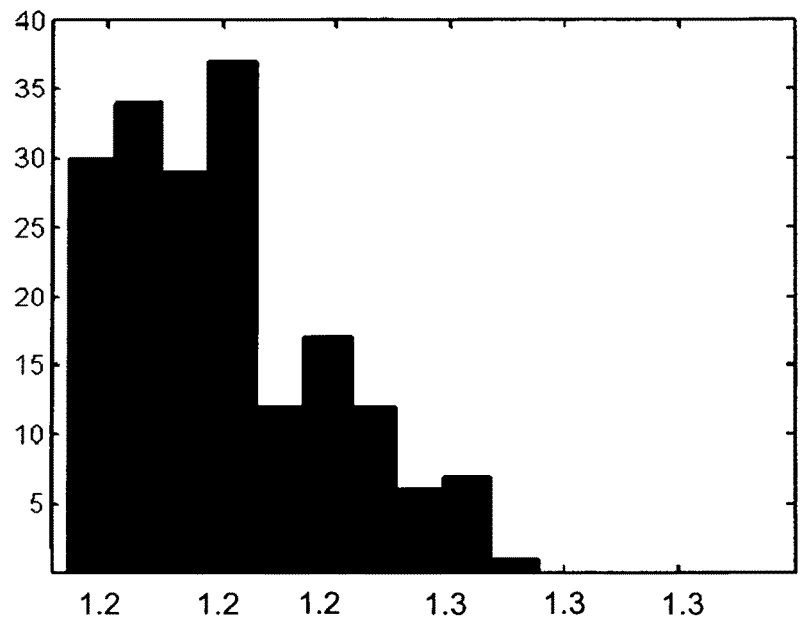
FIG. 4 is a histogram of AHDRFT values for (a) cancerous and (b) normal ROIs in our data (213 normal ROIs and 185 cancerous ROIs in 20 different frames of ultrasound data acquired from a 57 year old patient).
Figure 4B:
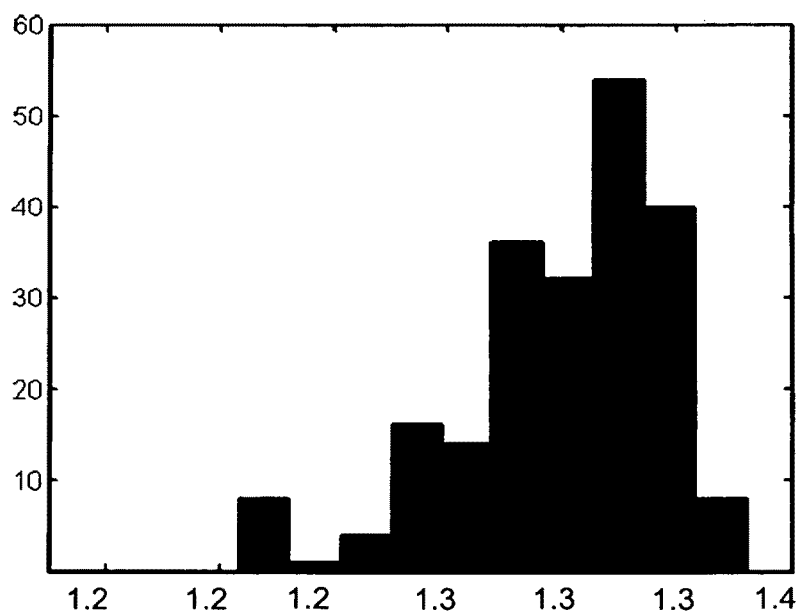

Single patient classification experiments: In the first set of experiments, we selected 213 normal ROIs and 185 cancerous ROIs in the data (based on the histopathology results). The cancerous samples were from two different lesions (one hypoechoic and one isoechoic) in two different parts of the prostate tissue of a 57 year old patient. The ROIs were selected from 20 different frames of ultrasound data. In each experiment, two thirds of the data samples were randomly selected for training and the rest were used for testing the trained network. FIG. 4 is a histogram of the AHDRFT values, showing a dramatic separation between the cancerous (a) and normal (b) ROIs. Table 1.2 summarizes the results. Accuracy, sensitivity and specificity values reported in each row are the average of 10 experiments performed with the feature vector described in column two on the ANN architecture described in column three (which was found to be the optimal architecture in the corresponding case). Table 1.2 shows that after including AHDRFT in the feature vector, a significant increase in the classification accuracy is witnessed (compare rows 1 and 5). It is also worth mentioning that adding AHDRFT improved the performance of the DBS and DRF set. While the two dimensional vector formed by DBS and DRF (row 2) does not show any significant improvement over texture feature results (row 1), adding AHDRFT considerably increases the accuracy (row 4). The overall best results were acquired by using the feature vector that contained all seven features (around 97% accuracy, row 6).

In an effort for further statistical validation of the results, we performed 200 rounds of training and testing each time with a random split of training and testing sets. We used the seven dimensional feature vector and an average accuracy of 93.8% was recorded.

TABLE 1.2

The performance of different groups of features. Addition of AHDRFT considerably increased the accuracy.

| Test | Features | ANN§ | Accuracy | Sensitivity | Specificity |
|---|---|---|---|---|---|
| 1 | mean, std, ku*, sk** | 4-15-15-1 | 87.4 | 87.7 | 84.0 |
| 2 | mean, std, ku, sk, DBS, DRF | 6-10-10-1 | 88.7 | 85.2 | 88.3 |
| 3 | DBS, DRF | 2-20-1 | 88.4 | 89 | 88.7 |
| 4 | DBS, DRF, AHDRFT | 3-10-10-1 | 94.2 | 93.2 | 94.3 |
| 5 | mean, std, ku, sk, AHDRFT | 5-10-10-1 | 93.9 | 94.5 | 93.4 |
| 6 | mean, std, ku, sk, DBS, DRF, AHDRFT | 7-20-1 | 96.4 | 95.4 | 97.1 |

*Kurtosis,
**Skewness,
§Structure of the best performing ANN, number of neurons in network layers are separated with "-".

Cross validation classification experiments: In the second set of experiments, the ANN of choice was trained with the data used in the previous experiment and tested on ROIs extracted from the data acquired on a second patient (50 cancer ROIs extracted from two different tumors and 54 ROIs extracted from the non-cancerous areas in the prostate of a 54 year old patient). An MLP with two hidden layers and 10 neurons in each hidden layer was used with the seven dimensional feature vector. The sensitivity of the tests was constantly equal to or higher than 98%. However, the specificity dropped to almost 70%. In other words, although all areas of cancer were identified, a high rate of false positives was witnessed. This result urged us to further investigate the corresponding regions of the actual prostate tissue. We observed that relatively large lesions of BPH were present in the areas labeled as normal in data acquired from the second patient. Although BPH tissue is not cancerous, it shows a different cellular structure (see FIG. 2(b)). The high rate of false positive detections is likely due to the fact that networks were not trained on such benign ROIs.

1.4 Discussion and Conclusions

One embodiment of this invention relates to a new method of detecting cancer using time series ultrasound RF data and a fractal analysis. In this example, we used the average Higuchi dimension of RF time series (AH-DRFT) for prostate cancer detection from ultrasound RF signals and acquired highly promising tissue classification results. Malignant prostate tissue is composed of irregularly shaped and distributed cellular networks. In search for an ultrasound-based parameter that can discriminate cancer from normal tissue by characterizing the scattering caused by different tissue types, we analyzed backscattered RF time series acquired from prostate glands of patients undergone prostatectomy. The Higuchi fractal dimension of these time series averaged over an ROI showed a meaningful statistical difference in cancer versus normal regions. In ANN-based classification experiments on data acquired from one patient, we acquired up to 97% accuracy. Furthermore, the neural networks trained with our proposed set of features on data acquired from one patient were almost perfectly capable of detecting all cases of cancer in the data acquired from another patient. The detection of normal tissues on the second patient resulted in a lower accuracy. Our investigation showed that this phenomena is due to the presence of areas with BPH in the prostate tissue which was not considered as a separate class in our training data.

The experimental results demonstrate the effectiveness of this embodiment for detecting and diagnosing prostate cancer, and suggest that it will be effective in detecting and diagnosing other cancers as well as non-cancerous abnormalities in biological tissue, and in detecting defects in non-biological materials.

Example 2

Detection of Prostate Cancer using Fourier Analysis 2.1 Introduction

In Example 1 we performed a study involving extracted prostate tissue from two prostatectomy patients, and used fractal dimension of RF time series to detect prostate cancer. The results showed that the fractal dimension of RF time series is superior to texture features extracted from ultrasound B-scan images in detection of prostate cancer. However, the specificity of detection was low. To overcome this limitation, data has been collected from human prostate tissue samples, and various features have been extracted from RF time series to increase the diagnostic value of the embodiments described herein. This example presents a new set of features extracted from the amplitude of the discrete Fourier transform (DFT) of RF time series. These features represent the frequency spectrum of RF time series using a small profile that consists of six parameters. The results show that, when used together, these six parameters are excellent features for detection of prostate cancer with a simple neural network classifier. The results include a mean accuracy of over 91%, with 92% sensitivity and 90% specificity, and the results have been validated using detailed malignancy maps acquired from histopathologic analysis of seven prostate specimens. The results show that acquisition and analysis of RF time series is an efficient approach for detection of prostate cancer.

2.2 Methods 2.2.1 Ultrasound and Histopathology Data

Figure 5:
FIG. 5 shows a typical histopathological map of prostate tissue used as a standard.

Ultrasound and histopathology data were collected from patients who choose prostatectomy as their treatment choice at Kingston General Hospital (Kingston, Ontario, Canada). Excised prostate specimens were suspended in a water bath, and scanned along cross-sections marked by a pathologist. The distance between the cross-sections was 4 mm. The RF ultrasound data was collected using a Sonix RP (Ultrasonix Inc., Vancouver, Canada) ultrasound machine which is capable of recording raw RF frames. A transrectal ultrasound probe model BPSL9-5/55/10 was used with the central frequency set to 6.6 MHz. To form the RF time series, a continuous sequence of 112 frames of RF data were acquired, at the rate of 22 frames per second, from each cross-section of the tissue. The prostate specimen was then dissected along the scanned cross-sections. The pathologist then examined the tissues under a microscope, and provided malignancy maps which were overlayed on the cross-section slides (FIG. 5). These maps were used as the standard to evaluate the performance of detection based on the features extracted from the acquired RF time series.

The process of registering the histopathology maps to the ultrasound frames was performed manually. In some cases, the boundaries of the prostate in the ultrasound images were blurred (many scanned cross-sections were discarded due to uncertainty in the registration process). The results reported in this example were obtained based on data from 15 cross-sections of prostate specimens acquired from seven patients. Tissue characterizing features were extracted from square Regions of Interest (ROI) of size 0.03 cm² which is equivalent to 8×48 samples in an RF data frame. 285 ROIs in cancerous areas and 285 ROIs in normal areas of the scanned cross-sections were identified. The methods described in this example were applied to these 570 ROIs.

2.2.2 Feature Extraction

Each region of interest in the dataset is represented with seven features. All these features were extracted from the RF time series described above.

DFT-based features: These included six features extracted from the amplitude of the DFT of RF time series averaged over an ROI. Each RF time series is a discrete signal of length N (N=112 frames in this example). We were interested in variations of this signal; therefore, features were extracted from the zero-meaned time series. The discrete Fourier transform of the time series $x_t$ can be described as ([23]):

$$X[k] = \frac{1}{N}\sum_{n=0}^{N-1} x_t[n]e^{-j(2\pi/N)kn} \quad (3)$$

where X is the DFT of the zero-meaned RF time series $x_t$, and N=112. DFT was computed using the fast Fourier transform (FFT) algorithm [21] as implemented in MATLAB™ (The Mathworks, Inc., Natick, Mass., U.S.A.).

Since the RF time series are real and have mean of zero, |X[0]|=0 and |X[k]|=|X[N−k]|, where || denotes amplitude of a complex number [22]. In other words, the frequency spectrum of RF time series is completely represented by N/2 or 56 values, namely |X[k]| where k=1, . . . , n/2. We average each of these 56 values over all RF time series corresponding to RF samples in one ROI. The averaged spectrum of the ROI (|X|ROI) was then normalized as follows:

$$|\hat{X}_{ROI}[k]|=|\overline{X}_{ROI}[k]|/\max(|\overline{X}_{ROI}[k]|) \quad (4)$$

This normalization process set the maximum of the averaged spectrum to 1 and enabled comparison of data from different ROIs. The six proposed RF time series features, listed below, were extracted from (|$\overline{X}_{ROI}$|) and are designed to represent the frequency spectrum through a few parameters. The first four features (S1, S2, S3 and S4) are the integral of (|$\overline{X}_{ROI}$|) in four quarters of the frequency range:

$$S1 = \sum_{k=1}^{N/8} |\hat{X}_{ROI}[k]| \quad (5)$$

$$S2 = \sum_{k=N/8+1}^{N/4} |\hat{X}_{ROI}[k]| \quad (6)$$

$$S3 = \sum_{k=N/4+1}^{3N/8} |\hat{X}_{ROI}[k]| \quad (7)$$

$$S4 = \sum_{k=3N/8+1}^{N/2} |\hat{X}_{ROI}[k]| \quad (8)$$

Figure 6A:
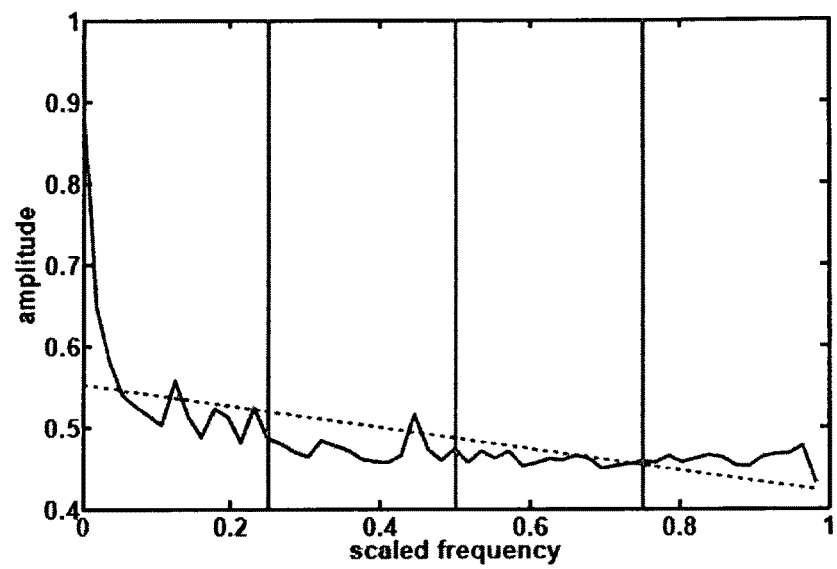
FIG. 6 shows plots of averaged normalized amplitude of discrete Fourier transform of RF time series from (a) normal and (b) cancerous ROIs. The slope and intercept of the linear regression of the frequency spectrum (dotted line) and the sum of the amplitude values in four different frequency bands (separated by vertical lines on the graphs) were used as features.
Figure 6B:
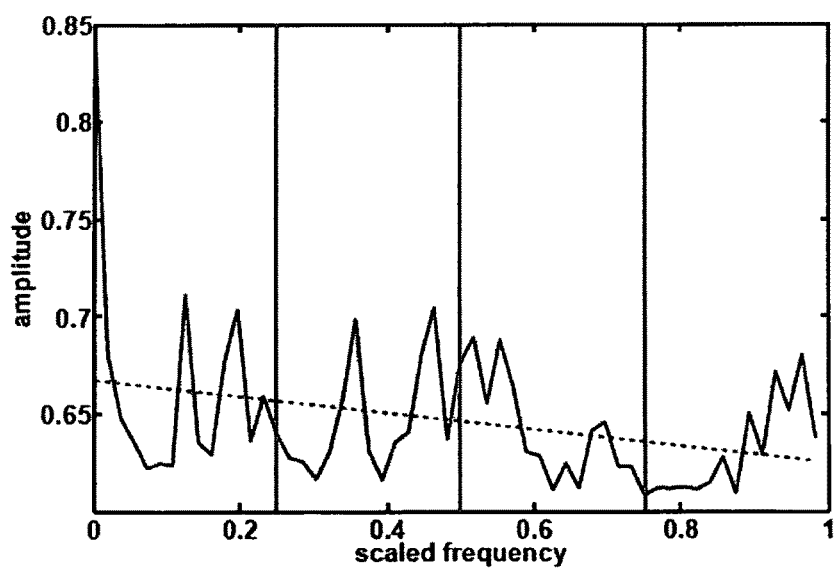

A regression line was fit to values of the spectrum (versus normalized frequency). The slope and intercept of this line were used as two more features. FIG. 6 illustrates the average spectrums over all normal (a) and cancerous (b) ROIs and clarifies the process of extracting S1-S4, spectral slope and intercept.

Fractal dimension: Example 1 describes our methodology for extracting the average fractal dimension of RF time series in a region of interest of tissue, which is based on Higuchi's algorithm. In order to extract the fractal dimension, Higuchi's algorithm computes mean length of the time series at different scales (up to a maximum scale $k_{max}$), plots a log-log graph of length versus scale, and measures the slope of the linear fit of this graph as the FD. We have shown that for tissue characterization based on FD, the algorithm works best with $k_{max}$=16. As mentioned earlier, the ROIs considered in this work are of size 8×48=384 in the RF data. The FD of each of the corresponding 384 time series in each ROI was computed, and these were averaged to acquire one feature per ROI (simply called FD in the rest of this example).

2.2.3 Classification Performance of Individual Features

To study the capability of the proposed features in detection of prostate cancer, the features were ranked individually. Each feature was considered as the sole characterizing parameter and used with a Bayesian approach to distinguish cancerous ROIs from normal ones. The Bayesian approach can be summarized as follows. If $\omega_n$ and $\omega_c$ represent ROIs from normal and cancerous tissues, and f represents the feature value of a given ROI (which we do not know what category it belongs to), Bayes rule states that the classification can be performed based on the following inequalities:

$$P(f|\omega_n)P(\omega_n) \gtrless P(f|\omega_c)P(\omega_c) \quad (9)$$

$P(w_n)$ and $P(\omega_c)$ are a priori probabilities (which can be simply calculated as the ratio of the number of ROIs in each category to the total number of ROIs). $P(f|\omega_n)$ and $P(f|\omega_c)$ are the probability distribution functions of feature values in normal and cancerous ROIs, respectively. For validation, the data was randomly partitioned in each category to 10 folds, probability density functions (PDFs) were evaluated on 90% of the data ROIs, the remaining 10% were classified based on Equation 9, and the procedure repeated for all 10 partitions of the data. The entire leave-10%-out process was repeated 200 times (each time with a new random partitioning of the ROIs to 10 folds), and the mean and standard deviation of the outcomes was recorded.

2.2.4 Neural Network Classification

Different combinations of the proposed features were used with feedforward neural networks in an effort to maximize accuracy in detection of cancerous lesions. Reported results were acquired on a network with two hidden layers; five neurons in each hidden layer with log-sigmoid transfer functions. A supervised learning strategy with Levenberg-Marquardt backpropagation training was used. For validation of the classification results, a leave- 10%-out training-testing methodology was followed. In other words, the network was trained using 90% of the data samples, the remaining 10% were classified, and procedure repeated for all 10 portions of the data. The entire leave-10%-out process was repeated 100 times, and the mean and standard deviation of accuracy, sensitivity and specificity were recorded.

2.3 Results and Discussion 2.3.1 Classification Results Using Individual Features Table 2.1 summarizes the ranking of individual features based on their performance in detection of prostate cancer ROIs as the sole feature. While the table provides sensitivity, specificity and accuracy, the ranking is based on accuracy. It is evident that the two features with high classification performance are spectral slope and the fractal dimension. In agreement with the results of Example 1, the classification based on FD resulted in very high sensitivity (94%) and low specificity (61%). In the case of spectral slope, the specificity is fairly high (83%) at the expense of sensitivity (77%). Among the other DFT-based features, the worst performance occurred when S1 and the spectral intercept were used. Both of these features characterize the low frequency components of the RF time series. S4, S3 and S2 have higher levels of tissue characterizing performance in decreasing order.

2.3.2 Neural Network-Based Classification Results

Table 2.2 presents the classification results acquired using different useful combinations of the selected features with the neural network classifier described above. The highest accuracy was 91.1%, acquired when a feature vector consisting of the six DFT-based features was used. This high accuracy was achieved while both sensitivity and specificity were very high (92.3% and 89.8%), a favorable outcome of a diagnostic test.

It is noted that addition of the FD to the DFT-based features did not add to the diagnostic value of the method (row 2). In other words, the six DFT-based features were sufficient for classification. Another interesting result was that although S1-S4 were not powerful features when used individually, the combination of all of them resulted in an efficient feature vector (the classification accuracy was 86.7% for a feature vector consisting of S1-S4). On the other hand, while FD and spectral slope were the two best performing individual features (Table 2.1), their combination did not provide a very high diagnostic accuracy (72.6%).

TABLE 2.1

Ranking of the seven features for accuracy in separation of normal and cancerous tissue using the Bayesian approach

| rank | feature | mean accuracy (std) | mean sensitivity (std) | mean specificity (std) |
|---|---|---|---|---|
| 1 | spectral slope | 80.1% (5.4) | 77.0% (2.0) | 83.5% (6.9) |
| 2 | FD | 76.9% (5.1) | 94.1% (3.0) | 61.9% (8.8) |
| 5 | S4 | 63.9% (6.1) | 57.5% (5.1) | 68.7% (7.4) |
| 4 | S3 | 62.3% (6.1) | 60.1% (5.3) | 63.9% (8.7) |
| 3 | S2 | 61.6% (6.9) | 57.5% (4.1) | 66.1% (9.0) |
| 6 | spectral intercept | 58.8% (6.9) | 54.2% (5.2) | 63.2% (4.6) |
| 7 | S1 | 57.3% (5.5) | 52.6% (5.2) | 63.2% (8.5) |

TABLE 2.2

Neural network classification results using different combinations of the seven features

| Feature vector (number of features) | mean accuracy (std) | mean sensitivity (std) | mean specificity (std) |
|---|---|---|---|
| spectral slope and intercept, S1-S4 (6) | 91.1% (2.7) | 92.3% (3.5) | 89.8% (4.2) |
| spectral slope and intercept, S1-S4, FD (7) | 89.4% (5.4) | 91.1% (6.7) | 87.2% (8.8) |
| S1-S4 (4) | 86.7% (3.8) | 88.5% (5.3) | 85.0% (6.0) |
| spectral slope and intercept (2) | 81.7% (3.9) | 80.7% (5.3) | 82.7% (8.4) |
| spectral slope and FD (2) | 72.6% (9.9) | 79.8% (8.3) | 65.2% (9.4) |

2.4 Conclusion

The above analysis showed that the six selected DFT-based features were self-sufficient for diagnosis of prostate cancer with high sensitivity and specificity. The analysis improves the performance of ultrasound-based methods for detection of prostate cancer. An advantage of the analysis is that the FFT algorithm reduces the computational complexity of calculating DFT-based features. Ongoing work investigates the effects of probe frequency, acquisition frame rate, and length of RF time series on the results of the analysis, and the use of phase information acquired from DFT of RF time series for tissue characterizing features.

Example 3

Tissue Characterization Using Fractal Dimension of High Frequency Ultrasound Rf Time Series 3.1 Introduction Ultrasound-based tissue characterization techniques rely on different patterns of scattering of ultrasound in tissues with dissimilar cellular microstructures. Although the exact physical mechanisms that govern these patterns are not well understood [24], microstructure-induced differences in ultrasound-tissue interaction are documented both at clinical (2-10 MHz) frequencies [25] and at higher frequencies [24, 26]. In other words, ultrasound radio frequency (RF) echoes contain information about tissue characteristics. However, it is challenging to disentangle this information from variations in the signal caused by system-dependent effects, such as mechanical and electrical properties of the transducer and diffraction effects due to the finite aperture of the transducer. This fundamental restriction of ultrasound-based tissue characterization techniques limits their sensitivity and specificity in diagnosis of cancer lesions [5, 20, 27].

The above examples demonstrate that if a specific location in tissue undergoes continuous interactions with ultrasound, the time series of the RF echo signals from that location carries "tissue characterizing" information. In other words, although variations in the intensity of one sample of RF echo over time are partly due to the electronic noise of the ultrasound machine or the errors caused during the beam-forming process, they depend on tissue characteristics as well. Use of high frequency ultrasound in this new approach may provide insight into this phenomenon. It is a well-known fact that at very high frequencies the scattering of ultrasound is primarily caused by cellular microstructure [24] as opposed to tissue macrostructure. Therefore, the dependence of the FD of RF time series on cellular microstructure should be more evident in high frequency data.

In this example, for the first time, RF echo time series acquired using high frequency ultrasound probes were analyzed. The data demonstrate that at these high frequencies, the differentiation of tissues based on FD of RF time series is closely related to differences in tissue microstructures. The FD of the RF times series was used to successfully distinguish segments as small as 20 microns of animal tissues of dissimilar microstructures with accuracies as high as 98%. Furthermore, the FD values calculated from the RF time series of different tissues showed statistically significant differences, far beyond the variations in FD values in one tissue type. These results suggest the presence of microstructure-related information in the RF time series, and provide a novel, effective method in diagnosing cancer, due to changes at the cellular level of the tissue during the formation of malignancy.

3.2 Methods

Figure 7:
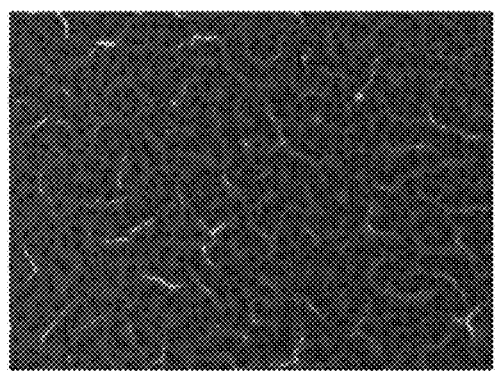
FIG. 7 shows photomicrographs (200× magnification) of the cellular structure of four tissue types (bovine liver, pig liver, chicken breast, bovine muscle) that were differentiated using an embodiment of the invention.
Figure 7:
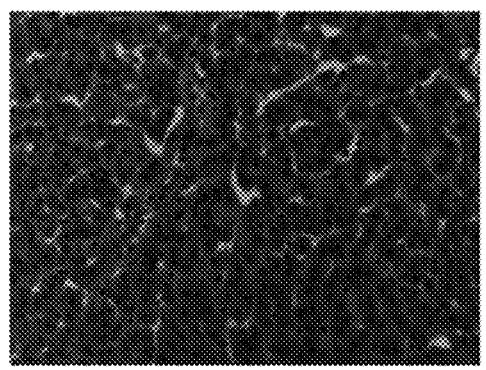
Figure 7:
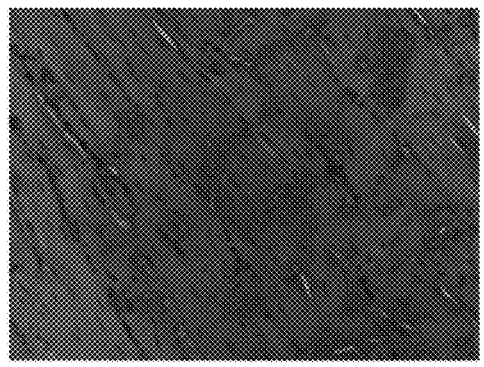
Figure 7:
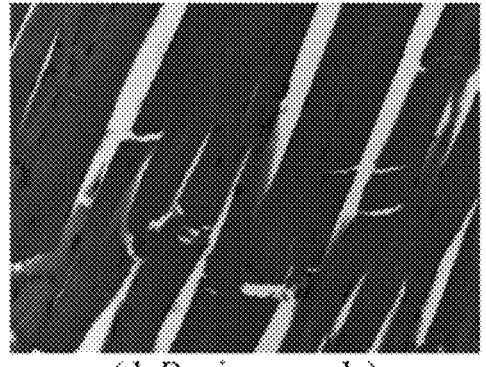

To study the tissue characterizing capabilities of RF echo time series acquired at higher frequencies, four different tissue types were used: bovine liver, pig liver, bovine muscle, and chicken breast. As illustrated in FIG. 7, the cellular structure of both bovine and pig liver are characterized by hepatocyte cells (the two are of slightly different shape and density), whereas bovine muscle and chicken breast both have fibrous structures formed by sarcomeres.

The high frequency ultrasound RF time series were collected using a Vevo 770 high resolution ultrasound system (VisualSonics Inc., Toronto, Canada) with two different probes of the 700-series RMV scanheads (see Table 3.1 for specifications). Each time series of RF data was formed by scanning a fixed spot of the tissue in A-mode (single lines of RF), with a depth of about 1 mm (equivalent to 512 samples of digital RF signal) 500 times at the rate of about 60 frames per second. Initially, we used the RMV711 scanhead to acquire two separate lines of RF time series from two different areas of each tissue type. Then, the data collection procedure was repeated using the RMV706 scanhead using the same tissue specimens.

TABLE 3.1

Specifications of the high frequency ultrasound scanheads.

| Model | Broadband frequency | Center frequency | Axial resolution |
|---|---|---|---|
| RMV711 | Up to 82.5 MHz | 55 MHz | 30μ |
| RMV706 | Up to 60 MHz | 45 MHz | 40μ |

3.2.1 Feature Extraction

Tissue types were characterized by the average of FDs computed for all the time series corresponding to RF samples in a Region of Interest (ROI). The high frequency data was acquired in A-mode. Therefore, ROIs were simply segments of RF lines (a segment with 10 samples was equivalent to 20 microns). We examined ROI sizes as small as a single RF sample up to 20 samples.

FD of time series originating from natural processes has been extensively studied as a parameter that quantifies nonlinear internal dynamics of complex systems [28, 29]. In such systems, the mechanisms of interaction that give rise to the output time series are not well understood. FD has been shown to have low sensitivity to noise-induced variations [30]. In the case of RF time series analysis, microstructural information is received along with noise-related variations. Therefore, FD was used to characterize the RF time series. Higuchi's algorithm [14] was used for computation of the FD of time series which can be summarized as follows: Each sample of the RF data forms a time series $\{X(1), X(2), \ldots, X(N)\}$ over sequential ultrasound frames, where N=500 for the high frequency RF data. From this time series, k new time series were constructed of form:

$$X_k^m : X(m), X(m+k), X(m+2k), \ldots, X\left(m + \left[\frac{N-m}{k}\right] \cdot k\right) \quad (10)$$

where k is the sampling time interval (which determines the scale, k<N) and m=1, 2, ..., k−1. Both m and k are integers. The length of each time series, $L_m(k)$, was defined as:

$$L_m(k) = \frac{1}{k} \times \left(\frac{N-1}{\left[\frac{N-m}{k}\right] \cdot k}\right) \times \sum_{i=1}^{\left[\frac{N-m}{k}\right]} \left| \begin{array}{c} X(m+ik) - \\ X(m+(i-1) \cdot k) \end{array} \right| \quad (11)$$

The average value of $L_m(k)$ over k sets, L(k), is the length of the time series at scale k. This procedure was repeated for each k ranging from 1 to $k_{max}$. A line was fitted to values of ln (L(k)) versus ln (1/k) and the slope of this line was considered as the FD. The number of samples, N, and the nature of the time series determine the optimal value of the parameter $k_{max}$. For this example, the value of $k_{max}$ was optimized based on the average classification accuracy acquired. $k_{max}$ values between 4 and 56 were examined. Feature extraction for each A-line involved computation of FD of 512 time series of length 500. The output of this process is referred to as a FD vector.

3.2.2 Bayesian Classification

All classification results reported herein were acquired with a Bayesian approach. If $\omega_1$ and $\omega_2$ represent ROIs from two categories of tissue in one of the classification experiments, and x represents the feature value of a given ROI (which we do not know what category it belongs to), Bayes' rule states that the classification can be performed based on the following inequalities:

$$P(x|\omega_1)P(\omega_1) \gtreqless P(x|\omega_2)P(\omega_2) \quad (12)$$

$P(\omega_1)$ and $P(\omega_2)$ are a priori probabilities (which can be simply calculated as the ratio of the number of ROIs in each category to the total number of ROIs in the two categories). $P(x|\omega_1)$ and $P(x|\omega_2)$ are the probability distribution functions (PDFs) of feature values in categories 1 and 2 respectively. A Gaussian PDF was fit to the distribution of the feature in each category.

A leave-10%-out validation methodology was followed for classification, in which the data was randomly partitioned in each category into 10 folds. The PDFs were evaluated on 90% of the data samples, and the remaining 10% were classified based on the evaluated PDFs, and the procedure was repeated for all 10 portions of the data. The whole leave-10%-out process Was repeated 200 times (each time with a random partitioning of the ROIs to 10 folds). The mean accuracies and standard deviations were recorded over these 200 trials.

3.3 Results and Discussion

FD vectors from the same tissue types: The first step in the analysis was to perform one-way analysis of variance (ANOVA) tests on pairs of FD vectors from the same tissue types. As Table 3.2 illustrates, when two FD vectors from the same tissue type were compared, the p-values in ANOVA tests were relatively large and the samples from two lines could not be separated (classification accuracies close to 50%). The ROI size used for classification was 20 microns (10 samples) and $k_{max}=16$.

TABLE 3.2

Comparison of two FD vectors from two RF lines of one tissue type.

| Tissue type | ANOVA p-value RMV711 | accuracy in separating ROIs from the two lines results on RMV711 - mean (STD) |
|---|---|---|
| Bovine liver | 0.47 | 52% (3.7) |
| Pig liver | 0.007 | 47% (3.9) |
| chicken breast | 0.0001 | 59% (3.1) |
| Bovine muscle | 0.68 | 53% (4.3) |

FD vectors from different tissue types ($k_{max}=16$): We performed the ANOVA tests on FD vectors of different tissue types (for all six possible pairs of tissue). Column 2 of Table 3.3 provides the p-values which were all virtually zero and showed that the vectors were statistically different in all six pairs.

Two separate FD vectors from each tissue type, computed from the data acquired on the RMV711 scanhead, were available. The two vectors of each tissue type were combined to acquire a single vector of length 1000 and the Bayesian approach described above was used to perform pairwise classifications. The results for these classification trials which were in single RF sample resolution are reported in column 3 of Table 3.3. It is interesting to note that even with this resolution, classification was successful when the two tissue types were from different microstructural categories (rows 1-4); however, when pig liver was compared with bovine liver (row 5) or the two fibrous tissue types were compared (row 6), the classification at this extremely high resolution produced lower accuracy.

For validation purposes, the classification process (at 20 micron resolution) was repeated on a similar dataset that was acquired on the RMV706 scanhead (which operates at a lower frequency and axial resolution). The results are reported in column 5, Table 3.3. In general, the overall outcome decreased in comparison with the RMV711 scanhead data (average overall: 83.2%). However, the same pattern of performance (excellent on different microstructures, moderate on similar microstructures) was observed. The overall decrease in the classification results can be explained by the lower axial resolution of the RMV706 scanhead.

Figure 8A:
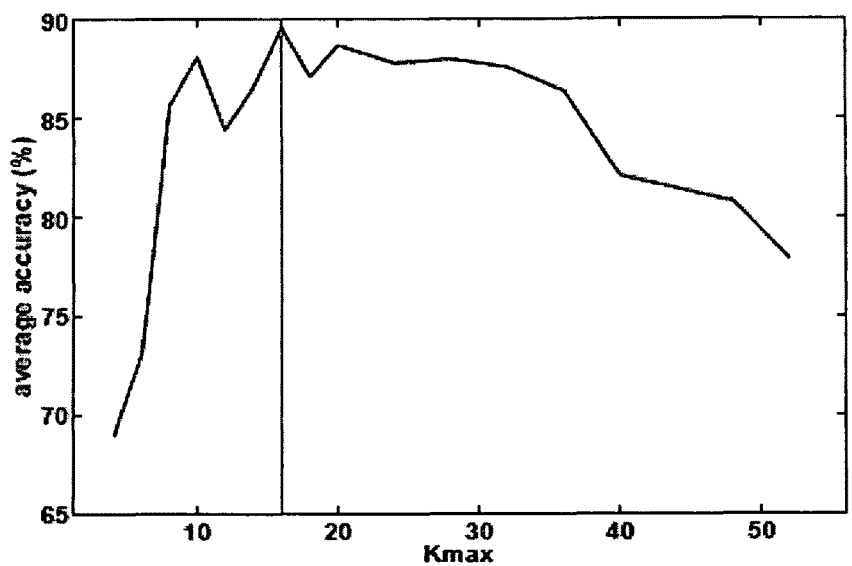
FIG. 8(a) is a plot of average classification accuracy over six pairs of tissue for different values of $k_{max}$ at resolution of 10 samples).
Figure 8B:
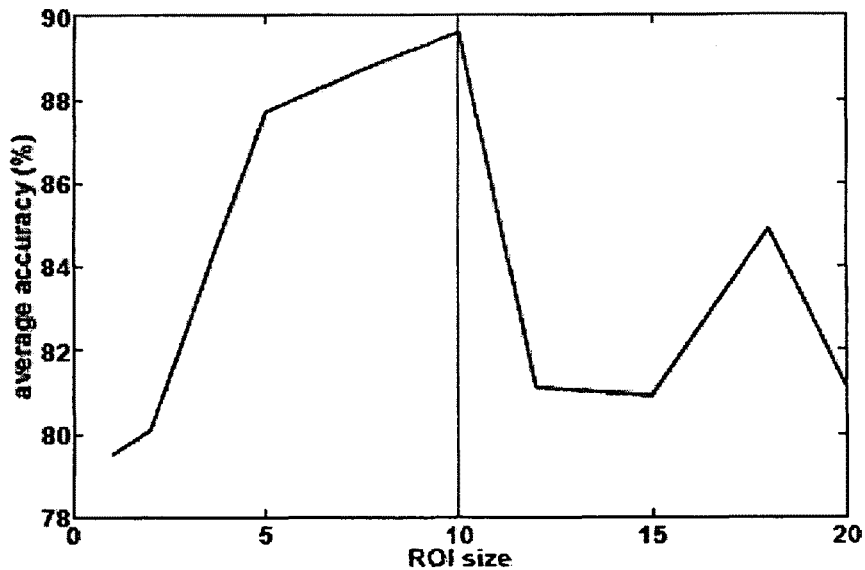
FIG. 8(b) is a plot of average classification accuracy over six pairs of tissue for different number of samples in an ROI ($k_{max}$=16).

Optimal $k_{max}$ value: Different possible values for $K_{max}$ (or maximum scaling level of the signal) were examined using Higuchi's algorithm. In FIG. 8(a), the average accuracy of tissue classification over six pairs of tissue types is plotted against the values of $k_{max}$ between 4 and 56. Values between 10 and 32 resulted in very similar outcomes. The Higuchi algorithm becomes increasingly computationally expensive for large values of $k_{max}$. We chose $k_{max}=16$ as a reasonably small number that also resulted in maximum accuracy. This is in agreement with the above findings regarding the optimal $K_{max}$ value on RF time series acquired from human prostate specimens.

Optimal ROI size: In general, it is reasonable to expect that the classification of ROIs of sizes smaller than the resolution of the ultrasound will be more challenging. As FIG. 8(a) illustrates, this is true for ROI sizes up to 20 microns (10 samples). However, we were limited by the size of the dataset, as increasing the ROI to over 10 samples meant that the Gaussian PDFs were estimated on less than 100 data points and tested on less than 10 points and therefore, the outputs were not reliable.

Comparison with results at 6.6 MHz: As previously noted, even at frequencies normally utilized on clinical machines (2-10 MHz), the RF time series contain tissue characterizing

TABLE 3.3

Comparison and classification of data from different tissue types

| Tissue types | p-value FD vectors RMV711 | mean (STD) 1 sample RMV711 | mean (STD) 10 samples RMV711 | mean(STD) 10 samples RMV706 |
|---|---|---|---|---|
| Bovine liver - chicken breast | 0 | 81.1% (2.5) | 92.2% (5.8) | 96.9% (3.5) |
| Bovine liver - bovine muscle | 0 | 84.1% (2.3) | 95.5% (4.0) | 93.7% (5.3) |
| Chicken breast - pig liver | 0 | 84.6% (2.3) | 96.0% (4.2) | 92.3% (5.3) |
| Pig liver - bovine muscle | 0 | 89.2% (2.1) | 98.2% (3.1) | 90.0% (6.4) |
| Bovine liver - pig liver | 0 | 73.7% (3.0) | 83.7% (7.1) | 65.1% (7.9) |
| Chicken breast - bovine muscle | $5.7 \times 10^{-13}$ | 64.1% (3.1) | 72.2% (8.9) | 63.1% (8.1) |
| Average over all six tissue pairs | | 79.5% | 89.6% | 83.2% |

Furthermore, the performance of our approach was examined at a lower resolution. Ten samples of each FD vector were examined to acquire vectors of length 50 (100 after combining the two lines from the RMV711 scanhead). Each element of these vectors represented an ROI of size 20 microns. The results of pairwise classification experiments at this level of resolution are presented in column 4, Table 3.3. For tissues in different microstructural categories, the mean accuracy was about 95% (rows 1-4); however, the accuracy dropped to about 80% for similar microstructures. The overall classification performance was 89.6%.

information. However, the maximum resolution is much lower. For comparison, we used a Sonix RP (Ultrasonix Inc., Vancouver, Canada) ultrasound machine to collect RF time series at 6.6 MHz from the same specimens that we had scanned at high frequencies. The temporal length of time series (number of frames taken from each cross-section) was 255 and the data was collected with a BPSL9-5/55/10 probe at the rate of 22 frames per second. ROIs of size 8×44 RF samples (equivalent to 0.03 cm$^2$) of the tissue were used in classification; 150 ROIs from each tissue type were available. Results reported in Table 3.4 show an overall accuracy of around 76.5%.

TABLE 3.4

Results using data acquired for probe center frequency of 6.6 MHz

| Tissue types | classification accuracy (STD) |
|---|---|
| Bovine liver - chicken breast | 82.9% (6.4) |
| Bovine liver - bovine muscle | 80.7% (6.8) |
| Chicken breast - pig liver | 71.4% (6.7) |
| Pig liver - bovine muscle | 74.8% (7.5) |
| Bovine liver - pig liver | 69.3% (5.3) |
| Chicken breast - bovine muscle | 79.6% (5.9) |
| Average over all six tissue pairs | 76.5% |

3.4 Conclusions

These findings demonstrate that tissue microstructure results in variations of the ultrasound RF time series. This concept can be used in ultrasound-based detection of fine differences and abnormalities in tissues, in diagnosing pathologic conditions such as cancer, and in detecting flaws, imperfections, and/or damage in other materials.

Other embodiments of the invention will be apparent to those skilled in the art. Such embodiments are within the scope of the invention and are covered by the appended claims.

REFERENCES

[1] Jemal, A.: Cancer statistics, 2004. CA: A Cancer Journal for Clinicians 54 (2004)8-29.

[2] American Cancer Society. [Online]. Available: http://www.cancer.org.

[3] Canadian Cancer Society. [Online]. Available: http://www.cancer.ca.

[4] Boyle, P.: Prostate specific antigen (PSA) testing as screening for prostate cancer: The current controversy. Annals of Oncology 9 (1998) 1263-1264.

[5] Scheipers, U., Ermert, H., Garcia-Schurmann, H. J. S. M., Sengeand, T., Philippou, S.: Ultrasonic multifeature tissue characterization for prostate diagnosis. Ultra-sound in Medicine and Biology 20 (2003) 1137-1149.

[6] Houston, A. G., Premkumar, S. B Pitts, D. E., Babaian, R. J.: Prostate ultrasound image analysis: localization of cancer lesions to assist biopsy. In: Proceedings of the Eighth IEEE Symposium on Computer-Based Medical Systems. (1995) 94-101.

[7] Lizzi, F. L., Greenebaum, M., Feleppa, E. J., Elbaum, M., Coleman, D. J.: Theoretical framework for spectrum analysis in ultrasonic tissue characterization. Journal of the Acoustic Society of America 73 (1983) 1366-1373.

[8] Schmitz, G., Ermert, H., Senge, T.: Tissue characterization of the prostate using Kohonen-maps. In: Ultrasonics Symposium. (1994) 1487-1490.

[9] Schmitz, G., Ermert, H., Senge, T.: Tissue-characterization of the prostate using radio frequency ultrasonic signals. IEEE Transactions on Ultrasonics, Ferroelectrics and Frequency Control 46 (1999) 126-138.

[10] Linzer, M., Norton, S. J.: Ultrasonic tissue characterization. Annual reviews of Biophysics and Bioengineering 11 (1982) 303-329.

[11] Waliszewski, P., Konarski, J.: Tissue as a self-organizing system with fractal dynamics. Advances in Space Research 28 (2001) 545-548.

[12] Ristanovic, D., Nedeljkov, V., Stefanovic, B. D., Miloevic, N. T., Grgurevic, M., Tulic, V.: Fractal and non-fractal analysis of cell images: comparison and application to neuronal dendritic arborization. Biological Cybernetics 87 (2002) 278-288.

[13] Pansera, F.: Fractals and cancer. Medical Hypotheses 42 (1994) 400.

[14] Higuchi, T.: Approach to an irregular time series on the basis of the fractal theory. Physica D: Nonlinear Phenomena 31 (1988) 277-283.

[15] Waag, R. C.: A review of tissue characterization from ultrasonic scattering. IEEE Trans. Biomed. Eng. BME-31 (1984) 884-893.

[16] Vorhoeven, J. T. M., Thijssen, J. M.: Potential of fractal analysis for lesion detection in echocardiographic images. Ultrasonic Imaging 15 (1993) 304-323.

[17] Sarkar, N.: An efficient differential box-counting approach to compute fractal dimension of image. IEEE Trans. Syst., Man, Cybern. 24 (1994) 115-120.

[18] Lee, W. L., Chen, Y. C., Hsieh: Ultrasonic tissues classification by fractal feature vector based on m-band wavelet transform. IEEE Transactions on Medical Imaging 22 (2003) 382-392.

[19] Theodoridis, S., Koutroumbas, L.: Pattern Recognition. Academic Press, San Diego, Calif. (1999).

[20] F. L. Lizzi, E. J. Feleppa, M. Astor, and A. Kalisz, "Statistics of ultrasonic spectral parameters for prostate and liver examination," IEEE Transactions on Ultrasonics, Ferroelectrics, and Frequency Control 44(4) (1997) 935-942.

[21] J. W. Cooley and J. W. Tukey, "An algorithm for the machine computation of the complex fourier series," Mathematics of Computation, 19 (1965) 297-301.

[22] A. V. Oppenheim, R. W. Schafer, and J. R. Buck, Discrete-Time Signal Processing, 2/E. Prentice Hall, 1999.

[23] R. H. Shumway and D. S. Stoffer, Time Series Analysis and Its Applications: With R Examples, $2^{nd}$ ed. Springer, 2006.

[24] Foster, F. S., Pavlin, C. J., Harasiewicz, K. A., Christopher, D. A., Turnbull, D. H.: Advances in ultrasound biomicroscopy. Ultrasound in Med. & Biol. 26 (2000) 1-27.

[25] Akashi, N., Kushibiki, Dunn, N. C. F.: Acoustic properties of selected bovine tissues in the frequency range 20-200 MHz. J. of Acoust. Soc. Am. 98(6) (1995) 3035-3039.

[26] Goss, S. A., Johnston, R. L., Dunn, F.: Compilation of empirical ultrasonic proper-ties of mammalian tissues. II. J. of Acoust. Soc. Am. 68 (1980) 93-108.

[27] Feleppa, E. J., Kalisz, A., Sokil-Melgar, J. B., Lizzi, F. L., Liu, T., Rosado, A. L., Shao, M. C., Fair, W. R., Wang, Y., Cookson, M. S., Reuter, V. E., Heston, W. D. W.: Typing of prostate tissue by ultrasonic spectrum analysis. IEEE Transactions on Ultrasonics, Ferroelectrics, and Frequency Control 43(4) (1996) 609-619.

[28] Accardo, A., Affinito, M., Carrozzi, M., Bouquet, F.: Use of the fractal dimension for the analysis of electroencephalographic time series. Biological Cybernetics 77(5) (1997) 339-350.

[29] Henderson, G., Ifeachor, E., Hudson, N., Goh, C., Outram, N., Wimalaratna, Percio, C. D., Vecchio, F.: Development and assessment of methods for detecting dementia using the human electroencephalogram. IEEE Transactions on Biomedical Engineering 53(8) (2006) 1557-1668.

[30] Shono, H., Goldberger, C. K. P. A. L., Shono, M., Sugimori, H.: A new method to determine a fractal dimension of non-stationary biological time-serial data. Computers in Biology and Medicine 30(4) (2000) 237-245.

The invention claimed is:

1. A method for determining one or more physical properties of a material, comprising:
   (I) obtaining a plurality of ultrasound data frames sequentially in time;
   wherein the plurality of ultrasound data frames is generated from an ultrasound signal received by one ultrasound transducer that is in one fixed relationship relative to the material and the ultrasound transducer is not subjected to intentional movement relative to the material;
   wherein each ultrasound data frame of the plurality of ultrasound data frames comprises a plurality of samples of the ultrasound signal reflected from and/or backscattered from the material;
   (II) selecting, from one ultrasound data frame of the plurality of ultrasound data frames, one or more samples of the ultrasound signal, wherein each sample is a scalar value corresponding to amplitude of the ultrasound signal at one position in the material;
   (III) selecting, from a second ultrasound data frame of the plurality of ultrasound data frames, one or more samples of the ultrasound signal, wherein each sample is a scalar value corresponding to amplitude of the ultrasound signal at the same position as each of the one or more samples in (II);
   (IV) repeating (III) to generate a time series of scalar values from a temporal sequence of the scalar values of the ultrasound signal;
   (Va) inputting the time series of scalar values to a classifier trained with data relating to known physical properties of one or more materials, wherein an output of the classifier is related to the temporal sequence of the time series of scalar values; or
   (Vb) subjecting the time series of scalar values to a discrete Fourier transform or a discrete wavelet transform to extract a plurality of spectral parameters, and inputting at least a portion of the plurality of spectral parameters to a classifier trained with data relating to known physical properties of one or more materials;
   (VI) outputting a result of the classifier;
   wherein the result of the classifier is indicative of one or more physical properties of the material.

2. The method of claim 1, wherein the ultrasound signal is selected from an A-mode, B-mode, M-mode, or 3-D ultrasound signal.

3. The method of claim 1, wherein the result of the classifier is indicative of the physical property of the material being normal or abnormal.

4. The method of claim 1, wherein the result of the classifier is a probability map or a probability score.

5. The method of claim 3, wherein the result of the classifier is indicative of severity of the abnormality in the material.

6. The method of claim 3, wherein the result of the classifier describes the presence of the abnormality in the material.

7. The method of claim 1, wherein the material is biological tissue.

8. The method of claim 7, wherein the biological tissue is human biological tissue.

9. The method of claim 8, wherein the material is biological tissue and the abnormality in the biological tissue is cancer.

10. The method of claim 9, wherein the cancer is associated with at least one of female genital tract (ovary, fallopian tube, uterus, cervix and vagina), male genital tract (prostate and testis), urinary tract (kidney, ureter and prostate gland), mediastinum and heart, gastrointestinal tract (small and large intestines, liver, pancreas, gallbladder and biliary system), breast, skin, nervous system, endocrine organs (thyroid gland, adrenal gland), head and neck region, lymph nodes, soft tissue, respiratory system (including lung), and combinations thereof.

11. The method of claim 9, wherein the cancer is prostate cancer.

12. The method of claim 6, wherein the material is biological tissue and the abnormality in the biological tissue is selected from benign tumour, infection, abscess, necrosis, infarct, and combinations thereof.

13. Programmed media for use with a computer, comprising:
   a computer program stored on non-transitory storage media compatible with the computer, the computer program containing instructions to direct the computer to perform the following steps:
   (I) obtain a plurality of ultrasound data frames sequentially in time;
   wherein the plurality of ultrasound data frames is generated from an ultrasound signal received by one ultrasound transducer that is in one fixed relationship relative to the material and the ultrasound transducer is not subjected to intentional movement relative to the material;
   wherein each ultrasound data frame of the plurality of ultrasound data frames comprises a plurality of samples of the ultrasound signal reflected from and/or backscattered from the material;
   (II) select, from one ultrasound data frame of the plurality of ultrasound data frames, one or more samples of the ultrasound signal, wherein each sample is a scalar value corresponding to amplitude of the ultrasound signal at one position in the material;
   (III) select, from a second ultrasound data frame of the plurality of ultrasound data frames, one or more samples of the ultrasound signal, wherein each sample is a scalar value corresponding to amplitude of the ultrasound signal at the same position as each of the one or more samples in (II);
   (IV) repeat (III) to generate a time series of scalar values from a temporal sequence of the scalar values of the ultrasound signal;
   (Va) input the time series of scalar values to a classifier trained with data relating to known physical properties of one or more materials, wherein an output of the classifier is related to the temporal sequence of the time series of scalar values; or
   (Vb) subject the time series of scalar values to a discrete Fourier transform or a discrete wavelet transform to extract a plurality of spectral parameters, and input at least a portion of the plurality of spectral parameters to a classifier trained with data relating to known physical properties of one or more materials;
   (VI) output a result of the classifier;
   wherein the result of the classifier is indicative of one or more physical properties of the material.

14. The programmed media of claim 13, wherein the computer program further directs the computer to:
   update the data relating to known physical properties of one or more materials by accepting further data relating to known physical properties of the material, or complementary data from subsequent analysis conducted on the material; and training the classifier according to the updated data relating to known physical properties of the material.

15. A system for determining one or more physical properties of a material, comprising:
   a computer;
   the programmed media of claim 13; and
   an ultrasound device for generating an ultrasound signal from the material.

* * * * *